United States Patent
Coulombe

(10) Patent No.: US 12,114,907 B2
(45) Date of Patent: Oct. 15, 2024

(54) PERCUTANEOUS COILED CATHETER DESIGN FOR GALLBLADDER CRYOABLATION

(71) Applicant: Medtronic CryoCath LP, Toronto (CA)

(72) Inventor: Nicolas Coulombe, Anjou (CA)

(73) Assignee: Medtronic CryoCath LP, Toronto (CA)

( * ) Notice: Subject to any disclaimer, the term of this patent is extended or adjusted under 35 U.S.C. 154(b) by 437 days.

(21) Appl. No.: 17/515,683

(22) Filed: Nov. 1, 2021

(65) Prior Publication Data

US 2023/0135845 A1    May 4, 2023

(51) Int. Cl.
| A61B 18/02 | (2006.01) |
| A61B 17/00 | (2006.01) |
| A61B 18/00 | (2006.01) |
| A61B 90/00 | (2016.01) |

(52) U.S. Cl.
CPC .... *A61B 18/02* (2013.01); *A61B 2017/00199* (2013.01); *A61B 2018/0022* (2013.01); *A61B 2018/00535* (2013.01); *A61B 2018/00577* (2013.01); *A61B 2018/00875* (2013.01); *A61B 2018/0212* (2013.01); *A61B 2018/0287* (2013.01); *A61B 2090/065* (2016.02)

(58) Field of Classification Search
CPC .......... A61B 18/02; A61B 2017/00199; A61B 2018/00535; A61B 2018/00577; A61B 2018/00875; A61B 2018/0212; A61B 2018/0287; A61B 2018/00214; A61B 2018/00232; A61B 2018/0025; A61B 2090/065
See application file for complete search history.

(56) References Cited

U.S. PATENT DOCUMENTS

| 9,168,080 B2 | 10/2015 | Wittenberger et al. |
| 9,554,848 B2 | 1/2017 | Stewart et al. |
| 10,441,338 B2 | 10/2019 | Mallin et al. |
| 10,898,694 B2 * | 1/2021 | Lalonde ................ A61B 18/02 |
| 2004/0167509 A1 | 8/2004 | Taimisto |
| 2008/0221651 A1 | 9/2008 | Dobak |
| 2012/0136350 A1 * | 5/2012 | Goshgarian ........ A61B 18/1492 606/41 |

(Continued)

FOREIGN PATENT DOCUMENTS

| WO | 2012019156 A1 | 2/2012 |
| WO | 2013090848 A1 | 6/2013 |
| WO | 2014028584 A1 | 2/2014 |

OTHER PUBLICATIONS

European Patent Office Extended Search Report for Application No. 22204215.2 dated Apr. 4, 2023 (8 pages).

*Primary Examiner* — Ankit D Tejani
*Assistant Examiner* — Joshua Brendon Solomon
(74) *Attorney, Agent, or Firm* — Michael Best & Friedrich LLP

(57) ABSTRACT

A medical system for ablating tissue within a gallbladder having a gallbladder wall includes a medical device. The medical device includes a shaft having a proximal portion and a distal portion opposite the proximal portion, and an inflatable treatment element coupled to the distal portion of the shaft and transitionable between a first deflated free-form configuration and a second inflated coiled configuration.

16 Claims, 6 Drawing Sheets

(56) References Cited

U.S. PATENT DOCUMENTS

| | | |
|---|---|---|
| 2014/0031804 A1 | 1/2014 | Lalonde |
| 2014/0180278 A1 | 6/2014 | Abboud et al. |
| 2014/0243780 A1* | 8/2014 | Leschinsky ........ A61B 18/1492 604/93.01 |
| 2015/0080875 A1* | 3/2015 | Kasprzyk ........... A61B 18/1815 606/33 |
| 2018/0036057 A1 | 2/2018 | Abboud et al. |
| 2020/0275968 A1 | 9/2020 | McGregor et al. |
| 2020/0360670 A1* | 11/2020 | Legum .................. A61B 18/04 |

* cited by examiner

PERCUTANEOUS COILED CATHETER DESIGN FOR GALLBLADDER CRYOABLATION

CROSS-REFERENCE TO RELATED APPLICATION n/a.

FIELD

The present technology is generally related to a device, system, and methods thereof, for ablation of the gallbladder based on an access method routinely used for drainage of the gallbladder.

BACKGROUND

Gall stone formation is a common cause of morbidity, affecting an estimated twenty million adults in the United States. Biliary colic develops in 1 to 4% of this population annually, with 20% of this group eventually developing inflammation of the gallbladder (cholecystitis). Surgical removal of the gallbladder, otherwise known as cholecystectomy, is the preferred treatment for biliary colic and cholecystitis, with more than 200,000 procedures performed annually. However, it has been postulated that ablation of the gallbladder may effectively treat these patients with less risk.

SUMMARY

The techniques of this disclosure generally relate to a device, system, and methods thereof, for ablation of the gallbladder based on an access method routinely used for drainage of the gallbladder.

In one embodiment, a medical system for ablating tissue within a gallbladder having a gallbladder wall includes a medical device. The medical device includes a shaft having a proximal portion and a distal portion opposite the proximal portion, and an inflatable treatment element coupled to the distal portion of the shaft and transitionable between a first deflated free-form configuration and a second inflated coiled configuration.

In another aspect of this embodiment, the medical device further includes a fluid supply lumen disposed within the shaft and extending within the inflatable treatment element. The fluid supply lumen defines a port.

In another aspect of this embodiment, the fluid supply lumen is made of a flexible material configured to readily contour and match the shape of the inflatable treatment element when the inflatable treatment element is transitioned between the first deflated free-form configuration and the second inflated configuration.

In another aspect of this embodiment, the port is defined along a length of the fluid supply lumen within the inflatable treatment element.

In another aspect of this embodiment, an electrode is disposed along an outer surface of the inflatable treatment element.

In another aspect of this embodiment, the electrode is configured to measure and record at least one impedance measurement signal.

In another aspect of this embodiment, the medical device is in communication with a console. The electrode is configured to transmit the at least one impedance measurement signal to the console.

In another aspect of this embodiment, the console is configured to determine a degree of tissue contact between the inflatable treatment element and the gallbladder wall based, in part, on the at least one impedance measurement signal.

In yet another embodiment, a medical device includes a plurality of shafts each having a proximal portion and a distal portion opposite the proximal portion, and an inflatable treatment element coupled to the distal portion of each shaft and transitionable between a first deflated free-form configuration and a second inflated coiled configuration.

In another aspect of this embodiment, the medical device further defines a major longitudinal axis, each inflatable treatment element is spaced apart from an adjacent inflatable treatment element along the major longitudinal axis when in the second inflated coiled configuration.

In another aspect of this embodiment, the medical device further includes a fluid supply lumen disposed within each shaft and extending within the inflatable treatment element coupled to each respective shaft. Each fluid supply lumen defines a port.

In another aspect of this embodiment, each fluid supply lumen is composed of a flexible material configured to readily contour and match the shape of each inflatable treatment element when transitioned between the first deflated free-form configuration and the second inflated configuration.

In another aspect of this embodiment, each inflatable treatment element is in fluid communication with a console.

In another aspect of this embodiment, each inflatable treatment element includes an electrode configured to measure and record at least one impedance measurement signal.

In another aspect of this embodiment, the electrode is configured to transmit the at least one impedance measurement signal to the console; and the console is configured to determine a degree of tissue contact between each inflatable treatment element and the gallbladder wall based, in part, on the at least one impedance measurement signal.

In yet another embodiment, a method of ablating an area of target tissue within a gallbladder having a gallbladder wall includes: positioning a medical device having an inflatable treatment element proximate to the area of target tissue, the inflatable treatment element transitionable between a first deflated free-form configuration and a second inflated configuration; and circulating refrigerant within the inflatable treatment element such that the inflatable treatment element transitions to the second inflated configuration and is at least in partial contact with an inner surface of the gallbladder wall.

In another aspect of this embodiment, the method further includes recording at least one impedance measurement signal, the at least one impedance measurement signal being recorded by an electrode; transmitting the at least one impedance measurement signal to a console; and determining a degree of tissue contact between the inflatable treatment element and the inner surface of the gallbladder wall based, in part, on the at least one impedance measurement signal.

In another aspect of this embodiment, the inflatable treatment element has an inner surface and an outer surface opposite the inner surface.

In another aspect of this embodiment, the inflatable treatment element further includes a fluid supply lumen disposed therein. The fluid supply lumen has a plurality of injection ports.

In another aspect of this embodiment, the refrigerant is delivered through plurality of injection ports towards the inner surface of the inflatable treatment element during the ablation phase.

In another aspect of this embodiment, the medical device further defines a major longitudinal axis and includes a plurality of inflatable treatment elements. Each inflatable treatment elements being spaced apart from an adjacent inflatable treatment element along the major longitudinal axis when in the second inflated coiled configuration.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
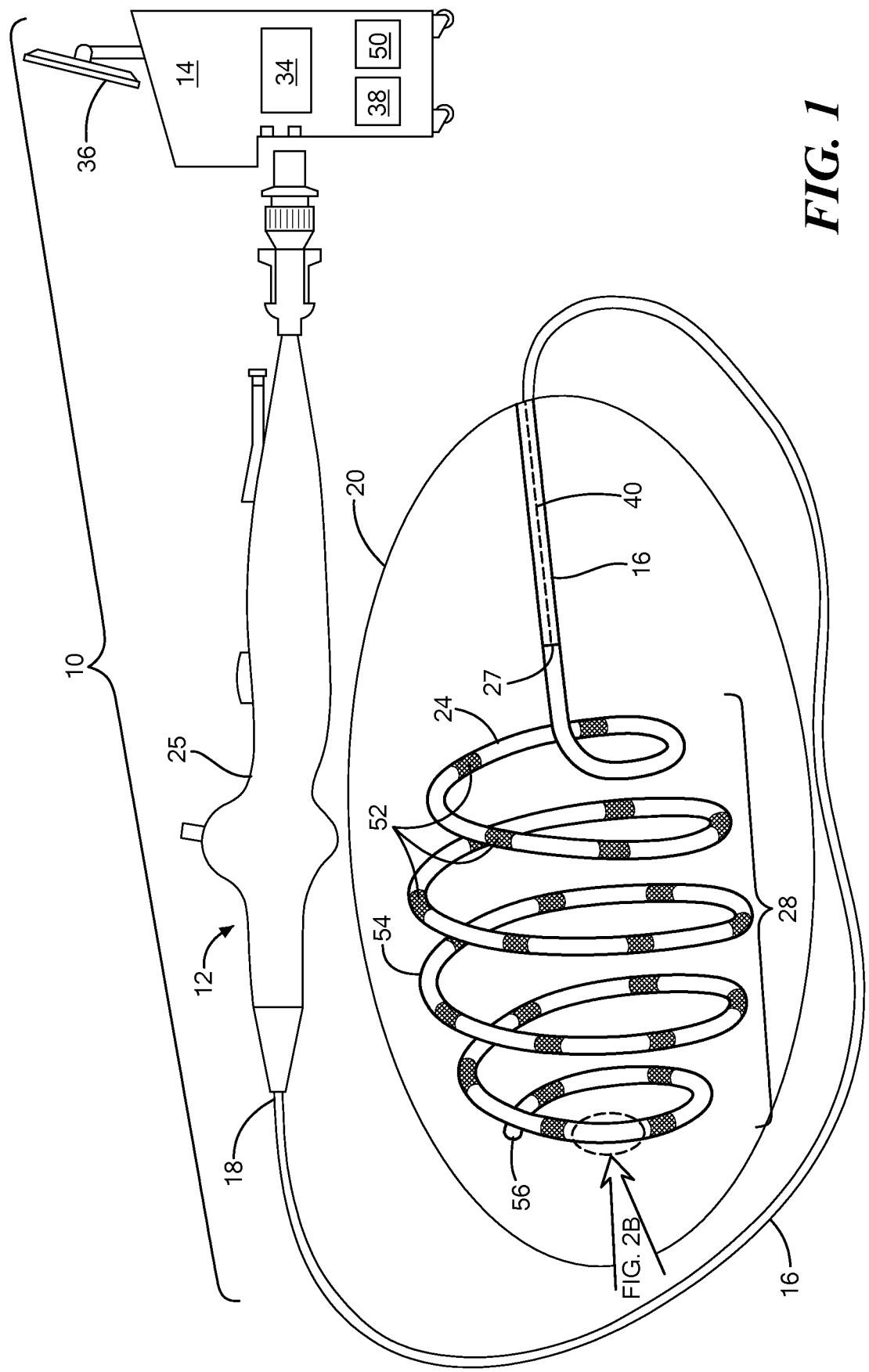
FIG. 1 shows a first configuration of a medical system constructed in accordance with the principles of the present application.

Referring now to the drawing figures where like elements have like reference numerals, FIG. 1 illustrates a medical system for ablating tissue within a gallbladder having a gallbladder wall and designated generally as "10". The medical system 10 may include a medical device 12 in electrical and/or fluid communication with a console 14. As shown in FIG. 1, the device 12 may have a shaft 16 that includes proximal portion 18 and a distal portion 20 opposite the proximal portion 18. Although not shown, it is to be understood that in some embodiments, the device 12 may be used together with a second medical device such as a guiding sheath 58 (discussed in more detail below) to assist in positioning the medical device 12 within a gallbladder. The shaft 16 of the medical device 12 is sized and configured to be passable through a patient's vasculature or abdomen, and/or positionable proximate to an area of target tissue within the gallbladder. The shaft 16 provides mechanical, electrical, and/or fluid communication between the inflatable treatment element 24 and a handle 25 of the device 12. The shaft 16 may be rigid and/or flexible to facilitate the navigation of the device 12 within the patient's body. Additionally, the device 12 further includes an inflatable treatment element 24. As shown in FIG. 1, the inflatable treatment element 24 is coupled to, and/or contiguous with, the distal end 27 of the shaft 16 so that the inflatable treatment element 24 may be passed through the patient's vasculature towards an area of target tissue within the gallbladder. The inflatable treatment element 24 is also flexible to allow for more desirable positioning proximate to an area of target tissue within the gallbladder or gallbladder wall. The inflatable treatment element 24 may be a tube or sleeve made of memory shape material that is pre-shaped to match the contour of an inner surface of the gallbladder wall. In some configurations, the inflatable treatment element 24 may be a nitinol or polyimide injection tube covered with a thin polymer balloon sleeve.

Continuing to refer to FIG. 1, the medical device 12 is in electrical and/or fluid communication with the console 14. The console 14 includes one or more controllers, processors, and/or software modules containing instructions or algorithms to provide for the automated operation and performance of the features, sequences, or procedures described herein. In one embodiment, for example, the console 14 includes processing circuitry 34 programmed or programmable to execute the automated or semi-automated operation and performance of the features, sequences, calculations, or procedures described herein. The processing circuitry 34 may include a memory and a processor. The memory is in electrical communication with the processor and includes instructions that, when executed by the processor, configure the processor to receive, process, or otherwise use signals from the device 12 and/or other system components. Still further, the console 14 may include one or more user input devices, controllers, speakers, and/or displays 36 for collection and conveying information from and to the user.

As shown in FIG. 1, the console 14 further includes a fluid supply reservoir 38 containing a cryogenic fluid, saline, coolant, refrigerant, or the like. The device 12 includes a flexible fluid supply lumen 40 extending through a lumen defined by the shaft 16 and within the inflatable treatment element 24. The fluid supply lumen 40 is in fluid communication with the fluid supply reservoir 38 and/or console 14. The processing circuitry 34 is configured and/or programmed to initiate a delivery of fluid such as air, saline, argon gas, refrigerant, or coolant, from the fluid supply reservoir 38 to the device 12 so that the inflatable treatment element 24 may be inflated or expanded.

Figure 2A:
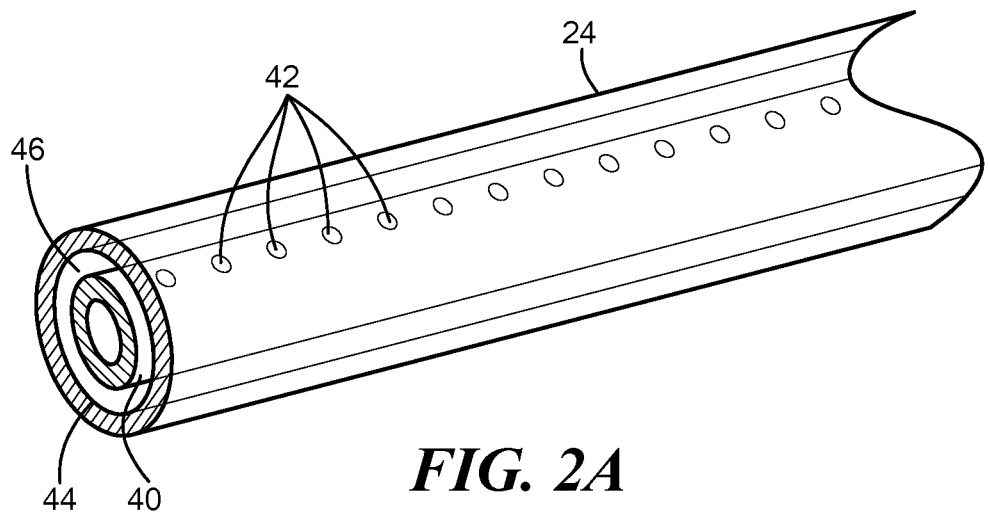
FIG. 2A shows an inflatable treatment element of the system of FIG. 1 in a deflated state.
Figure 2B:
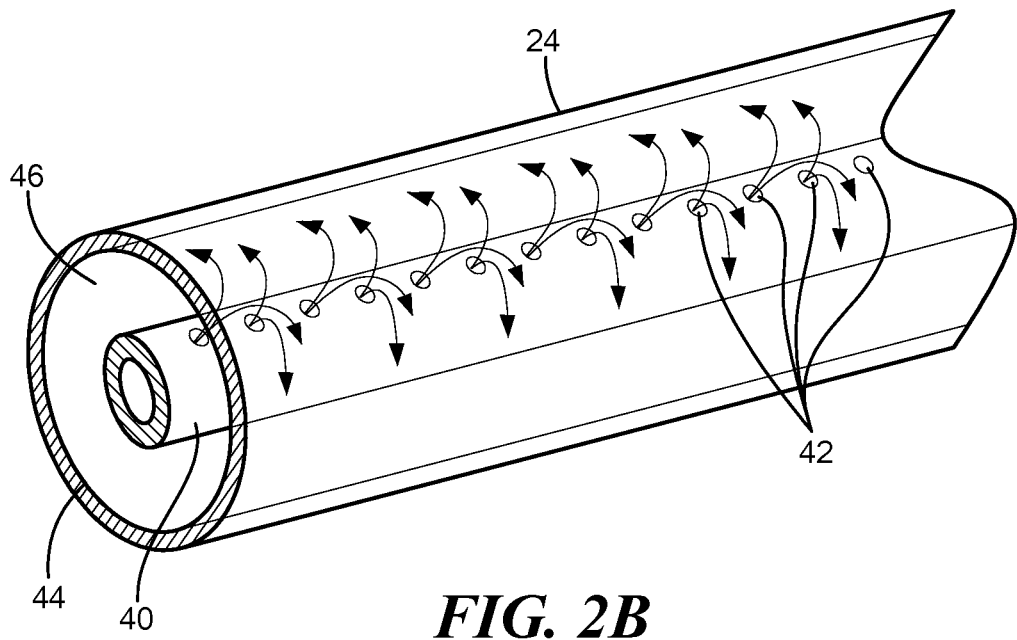
FIG. 2B shows the inflatable treatment element of FIG. 2 in an inflated state.

Now referring to FIGS. 2A-2B, the inflatable treatment element 24 includes the flexible fluid supply lumen 40 disposed therein. The fluid supply lumen 40 may define a plurality of injection orifices, or ports 42 to facilitate the dispersion of fluid towards an inner surface of the inflatable treatment element 24. In some configurations, as shown in FIG. 2A, the inflatable treatment element 24 is in a first deflated free-form state or configuration. When in the first deflated-free form configuration, the inflatable treatment element 24 may be more easily navigated within and through the patient's body and positioned within the gallbladder. When positioned within the gallbladder, the free-form configuration allows the inflatable treatment element 24 to be more freely maneuvered around any foreign and/or undesired objects such as, for example, gallstones present within the patient's gallbladder. Accordingly, the flexible fluid supply lumen 40 that is disposed within the inflatable treatment element 24 is also configured to readily contour and match the curvature, shape, or configuration of the inflatable treatment element 24. As fluid is dispersed towards the inner surface 44 of the inflatable treatment element 24, the dispersed fluid aggregates in a gaseous state within an inner chamber 46 defined between the fluid supply lumen 40 and the inner surface 44 of the inflatable treatment element 24. As more fluid is collected within the inner chamber 46, the inflatable treatment element 24 expands such that the diameter of the inflatable treatment element 24 is increased (as shown in FIG. 2B). In other words, the inflatable treatment element 24 is transitionable between a first deflated free-form configuration and a second inflated configuration. Additionally, when deflating the inflatable treatment element 24, a vacuum source or pump (not shown) disposed within the console 14, or in communication with the console 14, may initiate the return or suctioning of fluid from the inflatable treatment element 24 and through the lumen defined by the shaft 16. The suctioned fluid travels between a gap, chamber, or space defined between the inner wall of the shaft 16 and the fluid supply lumen 40. The fluid is suctioned back towards a fluid recovery reservoir and/or scavenging system (discussed in more detail below) disposed within, or external to, the console 14.

Continuing to refer to FIG. 1 and FIGS. 2A-2B, the treatment element 24 can be biased to a spiral, helical, or otherwise coiled shape, which can be predefined, or the treatment element 24 may be torqueable or otherwise deformable (e.g., by inflation of the treatment element 24). When in the second inflated configuration, the inflatable treatment element 24 may also define a coiled structure having a plurality of loops 28 (shown in FIG. 1) that are sized and configured to be in contact with the patient's gallbladder wall. Following the completion of a treatment or ablation procedure, the dispersed fluid may pass from the inner chamber 46 of the inflatable treatment element 24, through the lumen of the shaft 16 towards the proximal portion 18, and to a fluid recovery reservoir 50 and/or scavenging system so that the inflatable treatment element 24 can return to its deflated free-form configuration.

Further, the fluid recovery reservoir 50 and/or scavenging system referenced to herein may be physically located within or external to the console 14 (as shown in FIG. 1). In one configuration, the console 14 includes the fluid supply reservoir 38, the fluid recovery reservoir 50 for recovering or venting expended fluid for re-use or disposal, and various control mechanisms. In addition to providing an exhaust function for the fluid supply, the console 14 may also include pumps, valves, controllers or the like to recover and/or re-circulate fluid delivered to the shaft 16 and/or the fluid pathways of the system 10. Further, the console 14 may include a vacuum pump for creating a low-pressure environment in one or more conduits within the device 12 so that refrigerant is drawn into the conduit(s)/lumen(s) of the shaft 16. However, as mentioned above, the fluid supply reservoir 38, the fluid recovery reservoir 50, or scavenging system may instead be separate from, but in communication with, the console 14.

Figure 3:
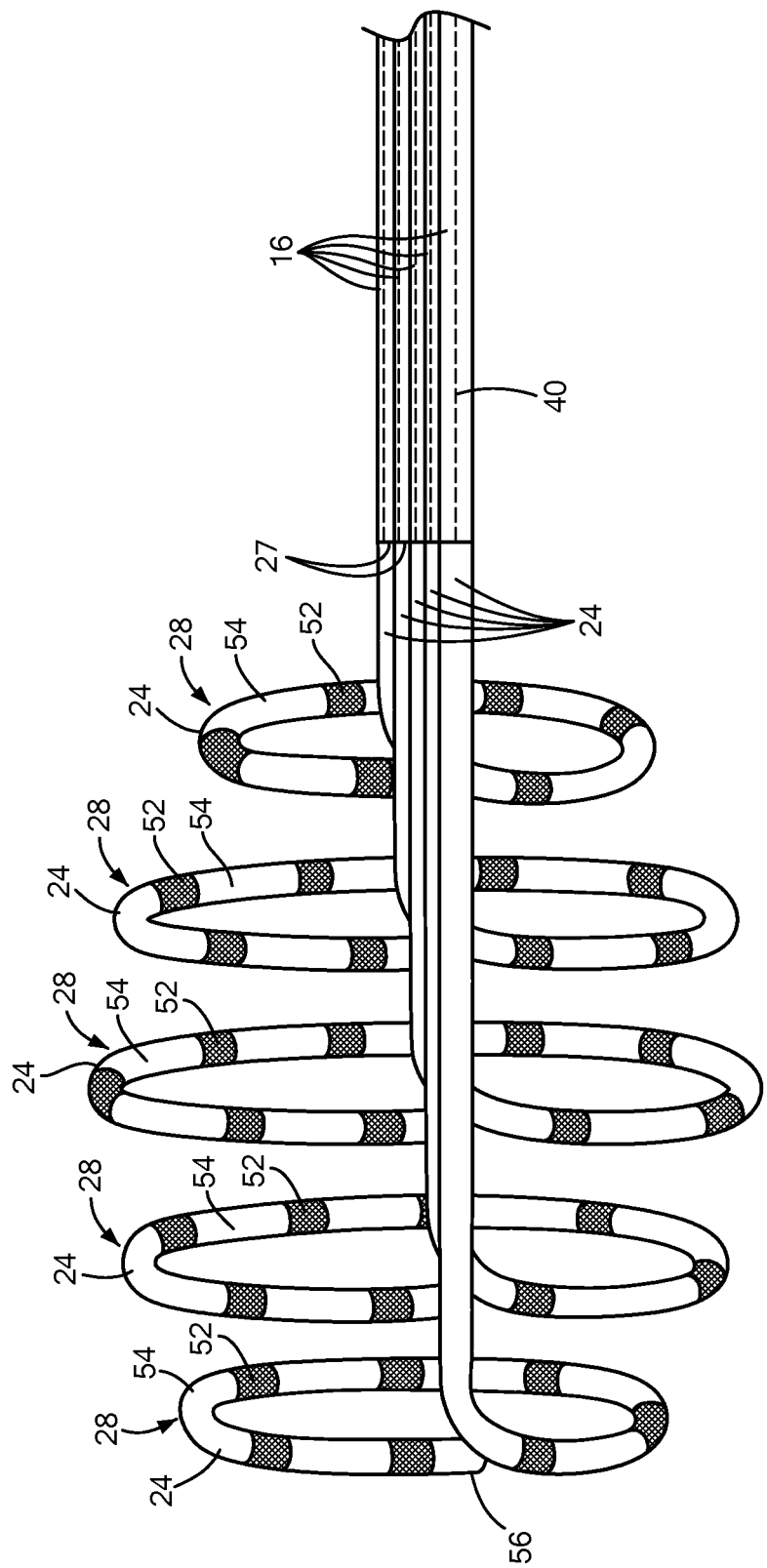
FIG. 3 shows a second configuration of the medical system constructed in accordance with the principles of the present application.

Now referring to FIG. 3, the medical device 12 includes a plurality of shafts 16 and a plurality of treatment elements 24 coupled to and/or contiguous with the distal end 27 of each respective shaft 16 to have an enhanced cooling distribution of refrigerant. In some configurations, each shaft 16 of the plurality of shafts is coupled, adhered, or otherwise bonded to at least one adjacent shaft 16. In other configurations, not shown, the plurality of shafts 16 may be disposed within a lumen having a plurality of isolated channels each sized and configured to receive one shaft 16 of the plurality of shafts. Each individual inflatable treatment element 24 can bring pressured refrigerant towards its distal tip 56 to maximize output over a shorter length or distance. In some embodiments, the device 12 may include five inflatable treatment elements 24 and five shafts 16. Each shaft 16 may have an independent fluid supply lumen 40 that extends through a respective inflatable treatment element 24 coupled to, and/or contiguous with, the distal end 27 of the shaft 16 and is in communication with the console 14. Each inflatable treatment element 24 is transitionable between the first deflated free-form configuration and the second inflated configuration. However, it is to be understood that the device 12 may include more or less than five inflatable treatment elements 24 as deemed necessary by the clinician to achieve a desired ablative efficacy or pattern. As shown in FIG. 3, when in the second inflated configuration, each inflatable treatment element 24 may define at least one loop 28 or spiral that is sized and configured to approximate or substantially match the curvature of the gallbladder wall.

Continuing to refer to FIG. 3, each inflatable treatment element 24 may be spaced apart from an adjacent inflatable treatment element 24 so that no two inflatable treatment elements are in physical contact with each other. Further, the inflatable treatment elements 24 may be inflated such that each inflatable treatment element 24 has a diameter that is the same as or different than an outer diameter of another inflatable treatment element. For example, some embodiments having five inflatable treatment elements 24 defining five loops 28, one respective loop 28 may have an outer diameter that is larger or smaller than the outer diameter of the other remaining loops.

As shown in FIGS. 1 and 3, each inflatable treatment element 24 includes a plurality of electrodes 52 in communication with the console 14 and configured to monitor a quality, level, or degree of contact between each inflatable treatment element 24 and the area of target tissue within the gallbladder wall and the growth of ice on the target tissue during a cryoablation procedure. Cryoablation may be referred to as the treatment of target tissue with thermal energy, and in particular, involves delivering cryogenic fluid to the inflatable treatment element 24 at a low enough temperature to extract heat from the target tissue, thereby ablating the target tissue. During or following the cryoablation procedure, some or all of the plurality of electrodes 52 may transmit an impedance signal to the area of target tissue within the gallbladder wall and measure or record a subsequent response indicative of the biological electrical activity within the area of target tissue. The measured response may be referred to as at least one impedance signal which may then be transmitted by the electrodes 52 to the console 14. The console 14 may either store the received impedance signal within the memory of the processing circuitry 34, or it may be used immediately for subsequent processing. For example, the processing circuitry 34 is configured and/or programmed to determine a degree of tissue contact between the inflatable treatment element 24 and the gallbladder wall based, in part, on the at least one impedance measurement signal, and relay the information to the patient and/or clinician via the 36 display, computer monitor, smartphone screen, or the like.

Continuing to refer to FIGS. 1 and 3, the plurality of electrodes 52 may be disposed along, coupled to, or otherwise printed on the outer surface 54 of the inflatable treatment element 24. In some embodiments, each electrode of the plurality of electrodes 52 may be a ring electrode or button electrode printed or coupled to the outer surface 54 of the inflatable treatment element 24. Each electrode 52 may be in electrical communication with a flexible tracing or wire (not shown) that is in electrical communication with the console 14. Alternatively, more than one electrode 52 may be in communication with a single tracing or wire. Also, in some embodiments, the plurality of electrodes 52 may be uniformly spaced apart along the outer surface 54. However, it is to be understood that the plurality of electrodes 52 may also be positioned such that a distance between each electrode 52 in a first pair of adjacent electrodes is different than a distance between each electrode 52 in a second pair of adjacent electrodes. In other words, in some configurations, the spacing between electrodes may be uniform, and in other configurations, the spacing between electrodes may not be uniform. The plurality of electrodes 52 may be flexible, stretchable, and/or may not be cinched down on the outer surface of the treatment element 24. In some such configuration, the electrodes 52 and/or the tracings may be printed in a zig-zag, spiral, helical, radial, or offset pattern along the length of the treatment element 24.

Figure 4A:
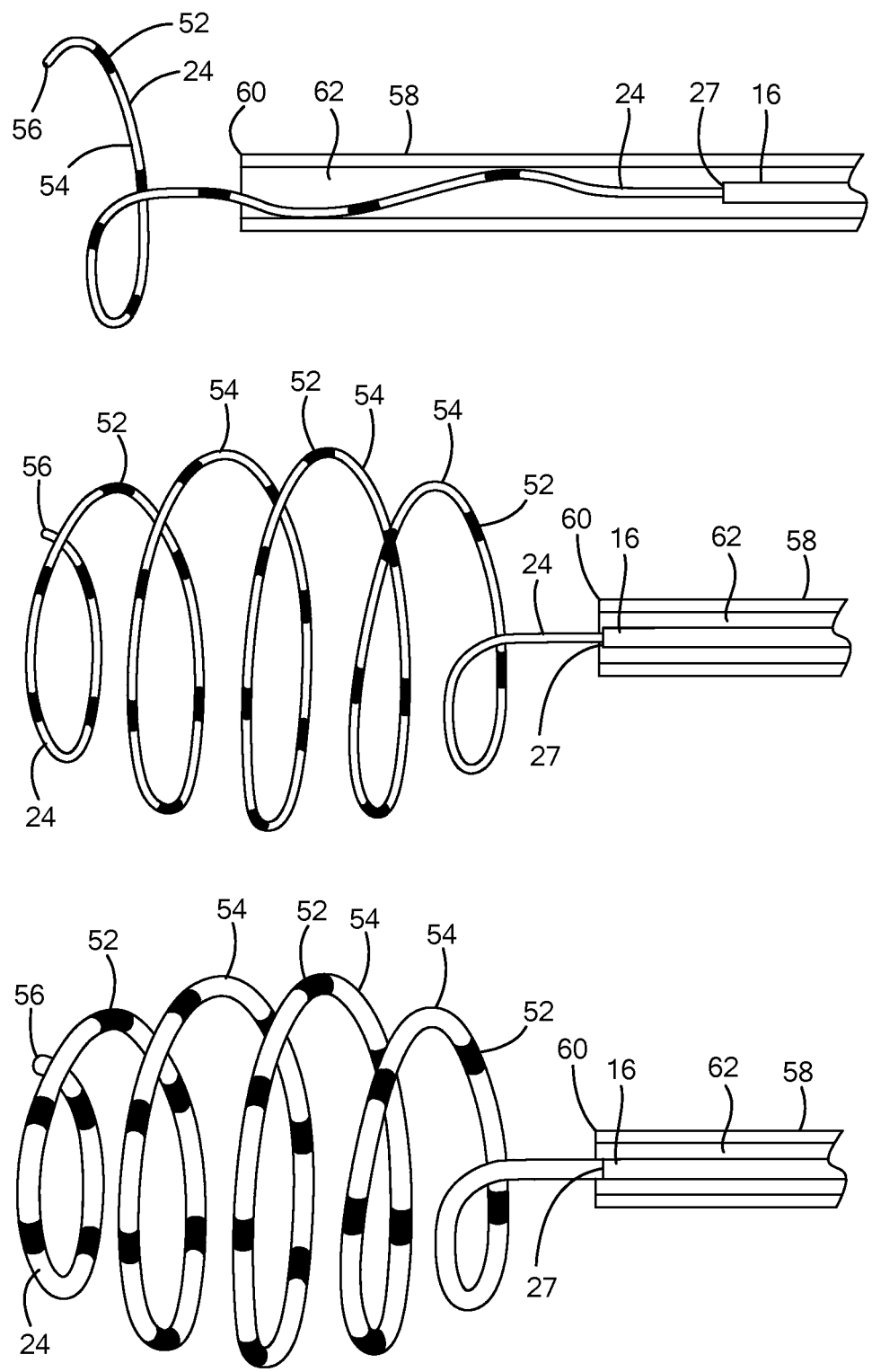
FIGS. 4A and 4B show the process of navigating the medical device of FIGS. 1-3 through a guide sheath, and inflating the inflatable treatment elements of the medical device of FIGS. 1-3.
Figure 4B:
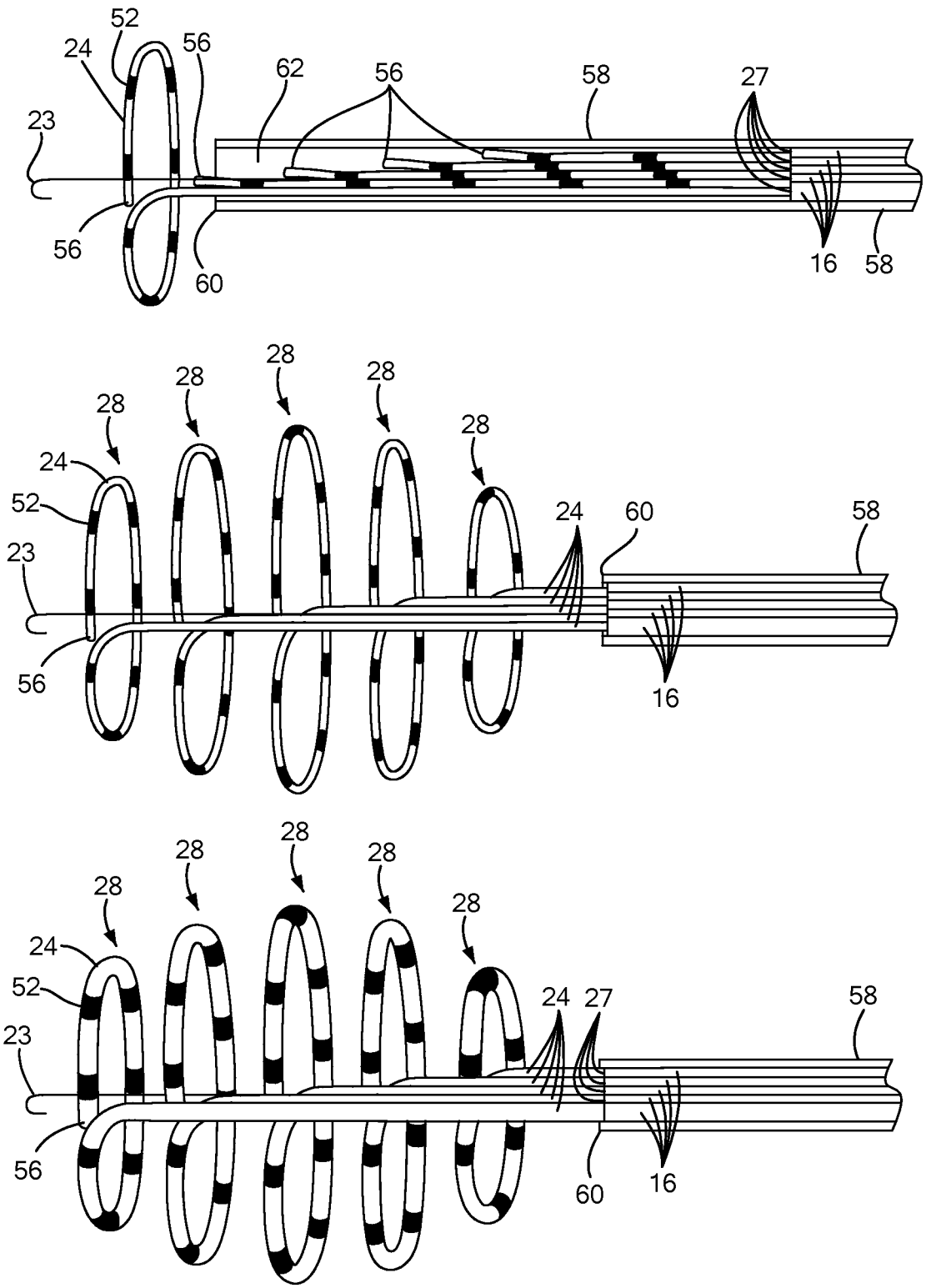

Now referring to FIGS. 4A-4B, in some embodiments, the medical device 12 may be used in combination with a second medical device that includes a guide sheath 58. The guide sheath 58 is an elongate body that is sized and configured to be passed through the patient's body and aids in positioning the medical device 12 within the gallbladder. This guide sheath 58 can be advanced after percutaneous access through the patient's chest, through the liver, through the gallbladder wall, and placement of a guidewire 23 within the gallbladder are performed. As shown in FIGS. 4A-4B, the guide sheath 58 includes a distal end 60 that defines an opening. The shafts 16 of the medical device 12 may be inserted and navigated through a lumen 62 of the guide sheath 58 until the distal end 27 of each shaft 25 is proximate to or coterminous with the distal end 60 of the guide sheath 58. Once navigated through the guide sheath 58, the plurality of inflatable treatment elements 24 are positioned near the area of target tissue within the gallbladder or gallbladder wall. Each inflatable treatment element 24 is biased to a spiral, helical, or otherwise coiled shape as it is inflated such that the outer surface of the treatment element 24 is in contact with multiple tissue surfaces within the gallbladder. Further, it is to be understood that although the guide sheath 58 is only illustrated in FIGS. 4A-4B, the guide sheath 58 may also be used with the device 12 that is shown in FIGS. 1-3 and described herein.

Figure 5:
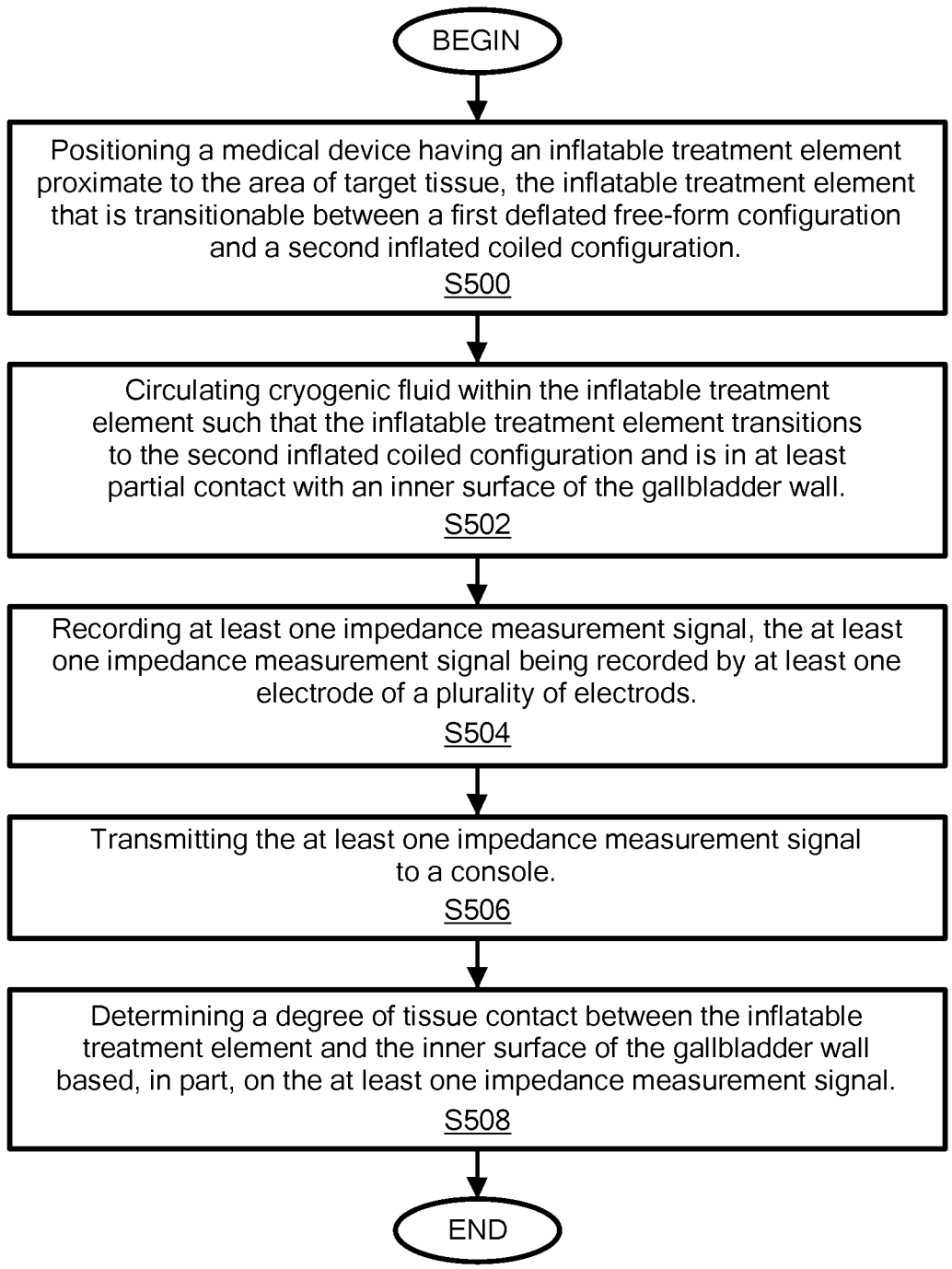
FIG. 5 is a flowchart illustrating an example method of using the medical system of FIGS. 1-4B.

Now referring to FIG. 5, in which an exemplary method of ablating an area of target tissue within a gallbladder having a gallbladder wall. The method includes first positioning a medical device 12 having an inflatable treatment element 24 proximate to the area of target tissue (Block S500). The inflatable treatment element is transitionable between a first deflated free-form configuration and a second inflated coiled configuration. Once the device 12 is in the desired position, cryogenic fluid may be circulated within the inflatable treatment element 24 during an ablation phase such that the inflatable treatment element 24 transitions to the second inflated configuration and an outer surface 54 of the inflatable treatment element 24 is at least in partial contact with an inner surface of the gallbladder wall (Block S502). During or after the ablation phase, at least one impedance measurement signal may be recorded or measured by at least one electrode of the plurality of electrodes 52 (Block S504). The recorded impedance measurement signal may then be transmitted from the electrode(s) 52 to the console 14 for processing and/or storage in the memory (Block S506). The console 14 then determines a degree of tissue contact between the inflatable treatment element 24 and the inner surface of the gallbladder wall based, in part, on the at least one impedance measurement signal (Block S508) and relays the relevant information to the patient and/or clinician via the external display unit 36.

Although the device 12 is described herein as operating to reduce the temperature of target tissue in order to ablate tissue within the gallbladder and gallbladder wall, it will be understood that the device 12 may also be used with one or more additional modalities, such as radiofrequency (RF) ablation, pulsed electric field ablation, ultrasound ablation, microwave ablation, or the like.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   a shaft having a proximal portion and a distal portion opposite the proximal portion;
   an inflatable treatment element coupled to the distal portion of the shaft and transitionable between a first deflated free-form configuration and a second inflated coiled configuration; and
   a fluid supply lumen disposed within the shaft and extending within the inflatable treatment element, the fluid supply lumen defining a port;
   wherein the fluid supply lumen is made of a flexible material configured to contour and match the shape of the inflatable treatment element when the inflatable treatment element is transitioned between the first deflated free-form configuration and the second inflated coiled configuration.

2. The device of claim 1, wherein the port is defined along a length of the fluid supply lumen within the inflatable treatment element.

3. The device of claim 2, further including an electrode disposed along an outer surface of the inflatable treatment element.

4. The device of claim 3, wherein the electrode is configured to measure and record at least one impedance measurement signal.

5. The device of claim 4, wherein the medical device is configured to be in communication with a console and wherein the electrode is configured to transmit the at least one impedance measurement signal to the console.

6. The device of claim 5, wherein the console is configured to determine a degree of tissue contact between the inflatable treatment element and a gallbladder wall based, in part, on the at least one impedance measurement signal.

7. A medical device, comprising:
a plurality of shafts each having a proximal portion and a distal portion opposite the proximal portion;
an inflatable treatment element coupled to the distal portion of each shaft and transitionable between a first deflated free-form configuration and a second inflated coiled configuration;
a fluid supply lumen disposed within each shaft and extending within the inflatable treatment element coupled to each respective shaft, each fluid supply lumen defining a port; and
wherein each fluid supply lumen is composed of a flexible material configured to contour to the shape of each inflatable treatment element when transitioned between the first deflated free-form configuration and the second inflated coiled configuration.

8. The device of claim 7, wherein the medical device further defines a major longitudinal axis, each inflatable treatment element is spaced apart from an adjacent inflatable treatment element along the major longitudinal axis when in the second inflated coiled configuration.

9. The device of claim 7, wherein each inflatable treatment element is in fluid communication with a console.

10. The device of claim 9, wherein each inflatable treatment elements includes an electrode configured to measure and record at least one impedance measurement signal.

11. The device of claim 10, wherein:
the electrode is configured to transmit the at least one impedance measurement signal to the console; and
the console is configured to determine a degree of tissue contact between each inflatable treatment element and a gallbladder wall based, in part, on the at least one impedance measurement signal.

12. A method of ablating an area of target tissue within a gallbladder having a gallbladder wall, the method comprising:
positioning a medical device having an inflatable treatment element proximate to the area of target tissue, the inflatable treatment element being transitionable between a first deflated free-form configuration and a second inflated coiled configuration, the inflatable treatment element including a fluid supply lumen composed of a flexible material configured to contour and match the shape of the inflatable treatment element when transitioned between the first deflated free-form configuration and the second inflated coiled configuration; and
circulating refrigerant within the inflatable treatment element such that the inflatable treatment element transitions to the second inflated coiled configuration and is in at least partial contact with an inner surface of the gallbladder wall.

13. The method of claim 12, further including:
recording at least one impedance measurement signal, the at least one impedance measurement signal being recorded by an electrode;
transmitting the at least one impedance measurement signal to a console; and
determining a degree of tissue contact between the inflatable treatment element and the inner surface of the gallbladder wall based, in part, on the at least one impedance measurement signal.

14. The method of claim 13, wherein the inflatable treatment element has an inner surface and an outer surface opposite the inner surface.

15. The method of claim 14, wherein:
the inflatable treatment element further includes a fluid supply lumen disposed therein, the fluid supply lumen having a plurality of injection ports; and
the refrigerant is delivered through the plurality of injection ports towards the inner surface of the inflatable treatment element during an ablation phase.

16. The method of claim 15, wherein the medical device further defines a major longitudinal axis and includes a plurality of inflatable treatment elements, each of the plurality of inflatable treatment elements being spaced apart from an adjacent inflatable treatment element along the major longitudinal axis when in the second inflated coiled configuration.

* * * * *